United States Patent [19]
Hitchcock et al.

[11] Patent Number: 5,930,125
[45] Date of Patent: Jul. 27, 1999

[54] COMPACT SOLID STATE KLYSTRON POWER SUPPLY

[75] Inventors: Roger N. Hitchcock, San Leandro; Michael J. Marziale, El Sobrante; Lance W. Thompson, San Leandro, all of Calif.

[73] Assignee: Siemens Medical Systems, Inc., Iselin, N.J.

[21] Appl. No.: 08/704,054

[22] Filed: Aug. 28, 1996

[51] Int. Cl.⁶ .................................................. H02M 3/335
[52] U.S. Cl. ................................................ 363/26; 363/89
[58] Field of Search .............................. 363/26, 89, 133, 363/134, 21; 219/715, 716, 761; 307/110

[56] References Cited

U.S. PATENT DOCUMENTS

| | | | |
|---|---|---|---|
| 4,302,651 | 11/1981 | Wills | 219/10.55 |
| 4,835,353 | 5/1989 | Smith et al. | 363/98 |
| 5,045,658 | 9/1991 | Smith | 219/10.55 |
| 5,083,093 | 1/1992 | Adler et al. | 328/65 |
| 5,181,160 | 1/1993 | Okamoto et al. | 363/97 |
| 5,321,235 | 6/1994 | Makino et al. | 363/98 |
| 5,483,122 | 1/1996 | Derbenev et al. | 315/505 |
| 5,764,002 | 1/1998 | Jennings | 315/408 |

OTHER PUBLICATIONS

Stephen R. Bird, "20 kW Inverter Flyback Charging System," Westinghouse Electric Corporation, 1979 pp. 25–31.
R. Richardson et al., "Modern Pulsed Magnetron Transmitters For Air Traffic Control Applications," EEV, 1992, pp. 19–22.
Skolnik, Merrill I., *Introduction to Radar Systems*, © 1962 by McGraw–Hill Inc., pp. 214–215.

*Primary Examiner*—Peter S. Wong
*Assistant Examiner*—Derek J. Jardieu

[57] ABSTRACT

A high voltage pulse generating circuit for powering klystrons, and the like. The circuit includes a source of D.C. power having positive and negative terminals, a flyback transformer having a primary winding and a secondary winding, the primary winding having first and second terminals for connection to the source of D.C. power, a sensor for generating a signal indicating the amplitude of the current in the primary winding, and a solid state switching circuit for coupling the source of D.C. power to the primary winding of the flyback transformer. The primary winding is coupled to the power source in response to a control signal, and decoupled from the power source when a predetermined level of current is detected in the primary winding.

17 Claims, 3 Drawing Sheets

COMPACT SOLID STATE KLYSTRON POWER SUPPLY

FIELD OF THE INVENTION

The present invention relates to power supplies, and more particularly, to a compact power supply for use in powering linear accelerators, and the like.

BACKGROUND OF THE INVENTION

Radiation-emitting devices are generally known and used, for instance as radiation therapy devices for the treatment of patients. A radiation therapy device generally comprises a gantry which can be swiveled around a horizontal axis of rotation in the course of a therapeutic treatment. A linear accelerator is located in the gantry for generating a high energy radiation beam for therapy. This high energy radiation beam can be an electron or photon (X-ray) beam. During treatment, this radiation beam is trained on one zone of a patient lying in the isocenter of the gantry rotation.

In this arrangement, radiation is generated by applying an electron beam to a target to generate x-rays. The electron beam is typically generated in a linear accelerator that is powered by a klystron based power supply having a power output in the 10 to 30 kW range. FIG. 1 is a block diagram of a medical linear accelerator showing major components and auxiliary systems. Power supply 10 provides D.C. power to modulator 12. Modulator 12 includes a pulse forming network and a switch tube known as hydrogen thyratron. A thyratron is a low pressure gas device with a thermionic cathode. Over time, the cathode depletes itself. Thus, a thyratron has an inherent wear out mechanism. The high voltage pulses from modulator 12 are flat-topped D.C. pulses of a few microseconds in duration. These pulses are delivered to magnetron or klystron 14 and simultaneously to electron gun 16. Pulsed microwaves produced in magnetron or klystron 14 are injected into accelerator tube 20 via waveguide system 22. At the proper instant, electrons, which are produced by electron gun 16, are also pulse injected into accelerator tube 20. High energy electrons emerge from accelerator tube 20 in the form of a beam of approximately 3 mm in diameter. These electrons can be fed to treatment head 24 as a straight beam or to treatment head 26 as a bent beam. If the electrons are sent to treatment head 26, the electrons are bent by, for example, bending magnet 28 through a suitable angle (e.g., 270 degrees) between accelerator tube 20 and the target.

Prior art power supplies for linear accelerators are large, heavy devices that significantly increase the cost and size of the medical treatment system. One typical prior art system utilizes a high voltage transformer/rectifier system to generate a 21 kV DC power source from a conventional three-phase 208 V power source. The high voltage DC source is then used to generate a 15 kV pulse that is converted to the required 150 kV pulse via a high voltage pulse transformer. The high voltage transformer/rectifier assembly typically weighs 500 lbs. and occupies 8 cubic feet. As a result, the power supply must be housed in a separate cabinet from the linear accelerator. In addition to increasing the floor space needed to house the accelerator system, this additional cabinet requires special power transmission lines to couple the klystron output to the linear accelerator which further increases the cost and complexity of the system. Finally, the sheer weight of the system increases the cost of shipping.

Broadly, it is the object of the present invention to provide an improved high voltage power system for powering klystrons and the like. It is a further object of the present invention to provide a high voltage power system that requires less space than prior art high voltage power systems. It is a still further object of the present invention to provide a high voltage power system that is significantly lighter than prior art power supply systems. These and other objects of the present invention will become apparent to those skilled in the art from the following detailed description of the invention and the accompanying drawings.

SUMMARY OF THE INVENTION

The present invention is a high voltage pulse generating circuit for powering klystrons and the like. In one embodiment, the invention is used in a radiation treatment device. The high voltage pulse generating circuit includes a source of D.C. power, a flyback transformer, a sensor and a solid state switching circuit. The source of D.C. power has positive and negative terminals. The flyback transformer has a primary winding and a secondary winding. The primary winding in the flyback transformer has first and second terminals for connection to the source of D.C. power. The sensor generates a signal indicating the amplitude of the current in the primary winding. The solid state switching circuit couples the source of D.C. power to the primary winding of the flyback transformer. The primary winding is coupled to the power source in response to a control signal, and decoupled from the power source when a predetermined level of current is detected in the primary winding.

DETAILED DESCRIPTION OF THE INVENTION

Figure 1:
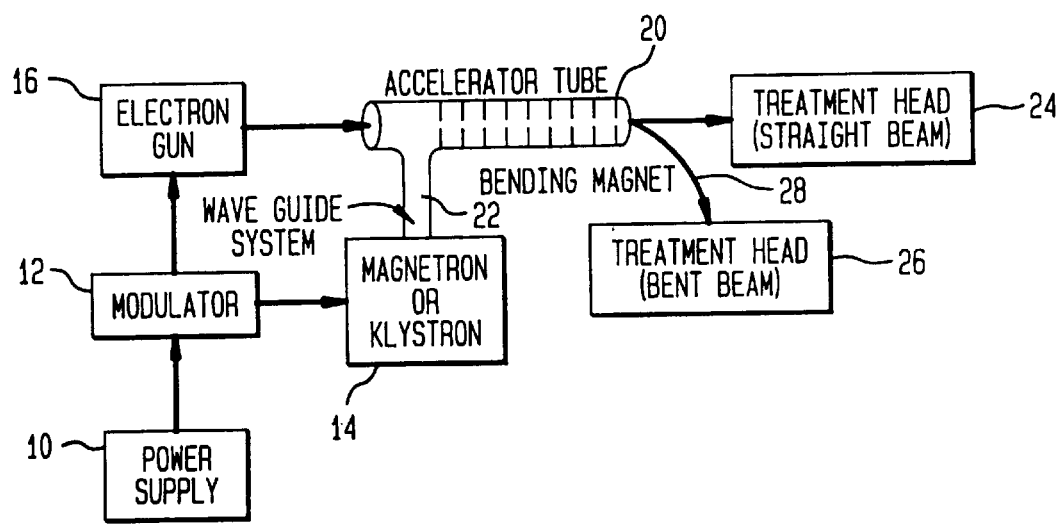
FIG. 1 is a block diagram of a medical linear accelerator showing major components and auxiliary systems.
Figure 2:
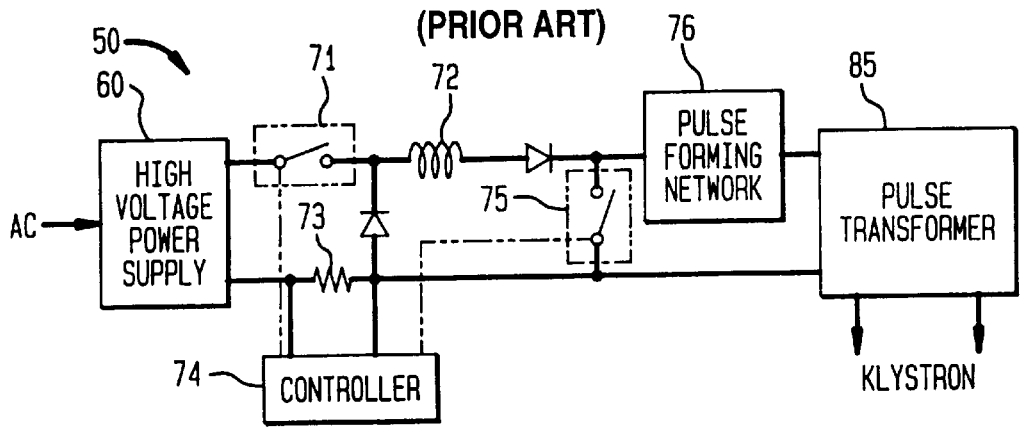
FIG. 2 is a block diagram of a typical prior art power supply system for operating a klystron for driving a linear accelerator.

The manner in which the present invention gains its advantages over the prior art may be more easily understood with reference to FIG. 2 which is a block diagram of a typical power system 50 for powering a klystron. Power system 50 converts 208 volt, 3 phase power to 15 kV, 1200 amp. pulses of approximately 5 $\mu$s duration. These pulses are stepped up to 150 kV by pulse transformer 85 whose output drives the klystron. The 15 kV pulses are generated by a pulse generating circuit that is powered by a 21 kV D.C. source. The 21 kV D.C. source is typically a high voltage transformer and rectifier assembly 60. As noted above this D.C. power supply typically occupies 8 cubic feet and weighs approximately 500 lbs.

The high voltage pulse generating circuit typically consists of an inductor 72 which resonantly charges a pulse forming network 76. The final pulse amplitude that is applied to the klystron is adjusted by controlling the amount of time a high voltage charge switch 71 is closed. The system measures the current flowing through a resistor 73 and the voltage at the pulse forming network 76 to determine the timing of the switch opening. The connection to the pulse forming network has been omitted from the drawing. A controller 74 utilizes the current and voltage measurements to control the switch closure duration. It should be noted that the range of adjustment in the final pulse amplitude that can be obtained with the inductor design shown in FIG. 2 is limited because only a portion of the energy of the final pulse is stored in inductor 72. It should also be noted that the conversion of the 208 volt power to a 21 kV D.C. source requires a substantial number of high voltage components that must operate at high power levels which require high voltage insulation and pose safety problems.

Figure 3:
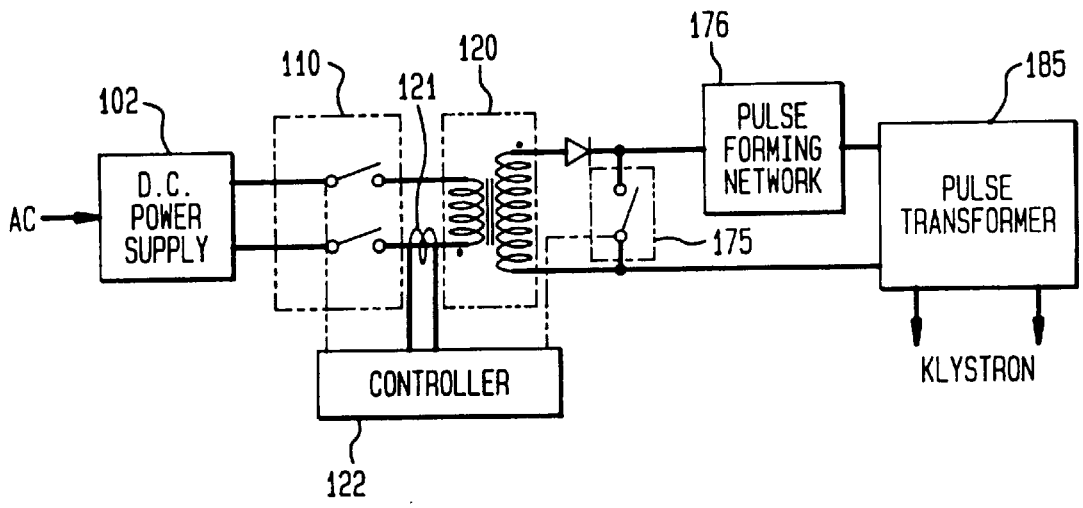
FIG. 3 is a block diagram of one embodiment of a high voltage power system according to the present invention.

FIG. 3 is a block diagram of a high voltage power system 100 according to the present invention. The present invention utilizes a flyback transformer 120 to power pulse forming network 176. Flyback transformer 120 is powered from a 300 volt D.C. power supply 102. This is a significant reduction from the 21 kV D.C. power supply used in the prior art. A solid state switch 110 is used to control the output voltage from flyback transformer 120. A controller 122 senses the current flowing in the primary of flyback transformer 120, as shown at 121. When the current reaches the desired level, switch 110 is opened, and the energy stored in flyback transformer 120 is transferred to pulse forming network 176. After pulse forming network 176 is charged, high voltage switch 175 is closed to discharge pulse forming network 176 thereby transferring the energy stored in pulse forming network 176 to the primary of pulse transformer 185. The operation of pulse forming network 176 and pulse transformer 185 are substantially the same as described above with respect to the typical klystron power system shown in FIG. 2.

It should be noted that flyback transformer 120 stores 100 percent of the energy that is later transferred to the klystron pulse. Hence, the present invention provides a greater range of control over the output pulse amplitude sent to the klystron. The control of the pulse amplitude is also simplified by the present invention. The pulse amplitude is controlled by opening switch 110 in response to a predetermined current being sensed in the primary of flyback transformer 120. Switch 110 operates at only 300 volts, in contrast to switch 71 shown in FIG. 2 which must operate at 21 kV. Hence, a significant savings in cost is achieved in addition to improved reliability and safety.

Further, since flyback transformer 120 is driven by a low voltage power source, the problems associated with the high voltage power supply are avoided. Power supply 102 requires approximately ¼ cubic feet of space and weighs only about 5 lbs (an 800 lb weight reduction). In addition, the lower operating voltage provides increased safety and reliability.

The basic flyback transformer design shown in FIG. 3 has been used in low power systems for some time. However, practical realizations of such a power supply for high power output have not been heretofore available. In particular, a practical implementation of switch 110 has been lacking. The vacuum tetrode used in the prior art contains an inherent wear out mechanism (the cathode), thus a solid state design is more desirable. In the present invention, switch 110 is implemented as a pair of insulated gate bipolar transistors (IGBTs).

Figure 4:
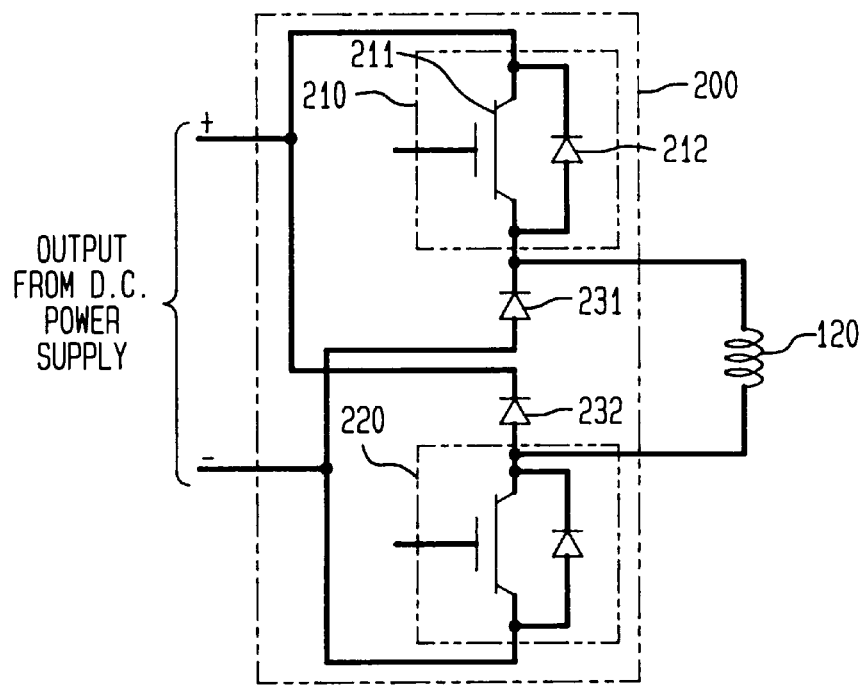
FIG. 4 is a schematic diagram of a power switch according to the present invention.

FIG. 4 is a schematic drawing of a power switch 200 according to the present invention. Power switch 200 utilizes two switching circuits shown at 210 and 220. Each switching circuit includes an IGBT 211 including a shunt diode 212. Switching circuits 210 and 220 are commercially available. Switching circuits 210 and 220 connect the D.C. power supply to the primary of flyback transformer 120. When switching circuits 210 and 220 disconnect the primary of flyback transformer 120 a reverse potential is generated across the primary winding. Clamping diodes 231 and 232 prevent this potential from damaging switching circuits 210 and 220, respectively. As a result, the power is recovered for use in the next pulse.

Figure 5:
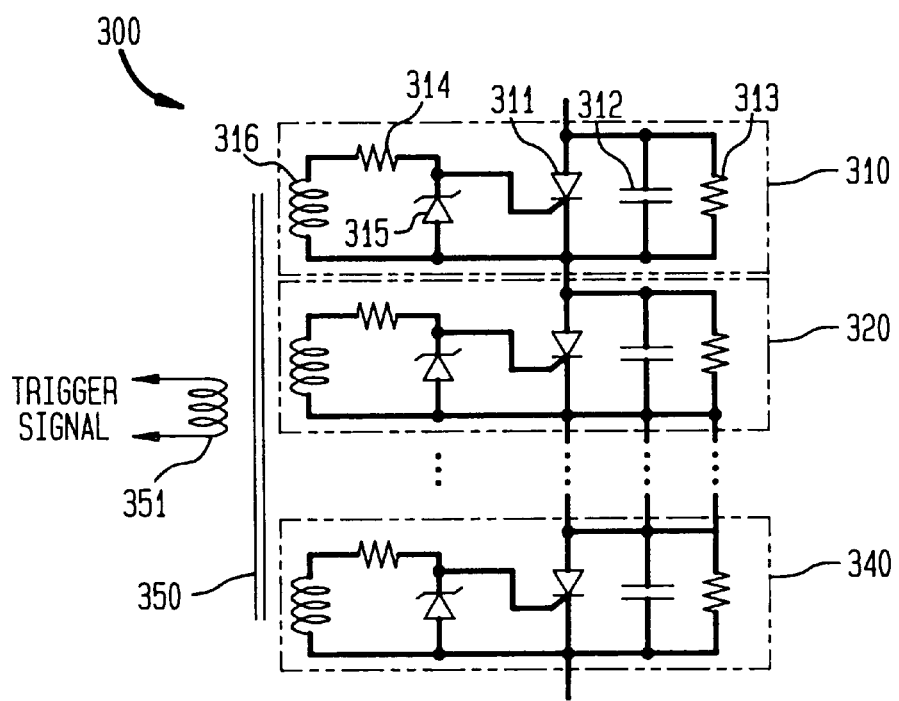
FIG. 5 is a schematic diagram of a high voltage switch according to the present invention.

In the preferred embodiment of the present invention, high voltage switch 175 (see FIG. 3) is implemented as a high voltage semiconductor controlled rectifier (SCR) stack (i.e., a number of SCRs in series). In prior art systems, the analogous switch is typically implemented with a gas thyratron which is less reliable and more costly than the SCR stack used in the present invention. The preferred embodiment of a high voltage switch according to the present invention is shown in FIG. 5 at 300. Switch 300 is constructed from a number of SCR stages connected in series. The first, second, and last stages are shown at 310, 320 and 340, respectively. Each stage includes an SCR in parallel with a resistor and a capacitor, the resistor and capacitor being connected between the anode and cathode of the SCR. For example, stage 310 includes SCR 311, capacitor 312 and resistor 313. The capacitors and resistors are also connected in series to form a voltage divider network. The voltage divider assures that the same voltage is applied across each of the SCRs when the SCRs are not conducting. In the absence of the voltage divider, differences in the impedances of the SCRs in the non-conducting state can lead to different potentials being realized across each SCR when the SCR stack is not conducting. This can result in one of the SCRs being subjected to a potential difference in excess of its breakdown voltage.

The stack is triggered by coupling a signal through the inductor 316 in each stage. These inductors are the secondary stage of a pulse transformer 350, the signal being applied to the primary 351 of pulse transformer 350. Each stage includes a resistor and zener diode that assures that the trigger voltage between the gate and cathode of the SCR in each stage are the same for each stage. The resistor and zener diode in the first stage are shown at 314 and 315, respectively.

Figure 6:
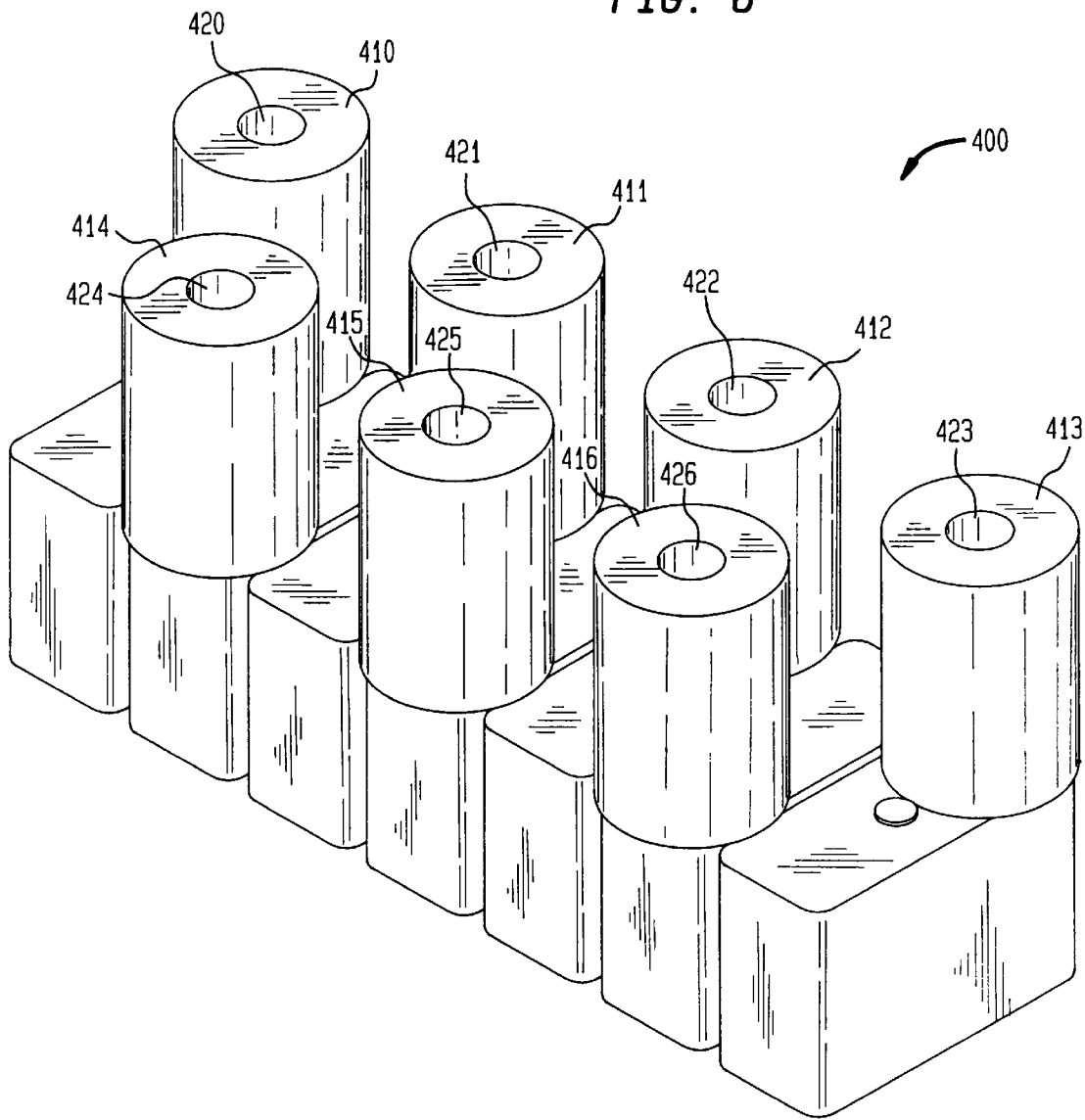
FIG. 6 is a block diagram of the pulse forming network in the preferred embodiment.

In the pulse forming network, the inductor design is improved. In particular, the inductance is made to be adjustable while the system is running. FIG. 6 is a block diagram of the pulse forming network in the preferred embodiment. Pulse forming network 400 includes inductors 410–416. Usually, in a pulse forming network, a clip is placed on the inductors and the system must be shut down to manually change the inductance. The inductance is changed to fine tune the wave shape provided by the pulse forming network. This shutting down of the system and reviewing the wave shape is typically done repeatedly until the desired wave shape is obtained. A specially trained individual requires approximately 1 hour to fine tune the wave shape. In contrast, the present design uses aluminum slugs 420–426 which are placed inside inductors 410–416. Each of aluminum slugs 420–426 can be moved up and down while the system is running to vary the inductance and fine tune the wave shape. Aluminum slugs 420–426 can be moved either manually or automatically. With this improved design, fine tuning takes approximately 3 minutes.

What is claimed is:

1. A high voltage pulse generating circuit, comprising:
   a source of D.C. power having positive and negative terminals;

a flyback transformer having a primary winding and a secondary winding, the primary winding having first and second terminals for connection to the source of D.C. power;

sensing circuitry for generating a signal indicative of current flowing in the primary winding, the signal indicating the amplitude of the current; and a solid state switching circuit for coupling the positive and negative terminals of the source of D.C. power to the first and second terminals of the primary winding of the flyback transformer in response to a control signal and for decoupling the D.C. power source from the primary winding in response to the signal indicating that a predetermined level of current is flowing in the primary winding, the solid state switching circuit comprising at least one conduction path for directing energy stored in a leakage inductance associated with the flyback transformer into the D.C. power source.

2. The high voltage pulse generating circuit of claim 1, further comprising:

a pulse forming network coupled to the first and second terminals of the secondary winding; and a high voltage switch for shorting the pulse forming network in response to a shorting signal.

3. The high voltage pulse generating circuit of claim 2, wherein the high voltage switch includes a plurality of SCR stages, each SCR stage comprising an SCR, a resistor, and a control signal generator, the SCR having an anode, a cathode, and a gate, the SCR conducting current from the anode to the cathode in the presence of a control signal generating a potential between the gate and the cathode, the control signal being generated by the control signal generator, the resistor being connected between the anode and cathode, the stages being connected such that the SCRs are connected in series.

4. The high voltage pulse generating circuit of claim 3, wherein the control signal generator in each the stage comprises a secondary winding of a pulse transformer, each said secondary winding being coupled to a common primary winding.

5. The high voltage pulse generating circuit of claim 1, wherein the solid state switching circuit comprises first and second IGBTs, the first IGBT coupling the first terminal of the primary winding to the positive terminal of the source of D.C. power when the first IGBT is in a conducting state, and the second IGBT coupling the second terminal of the primary winding to the negative terminal of the source of D.C. power when the second IGBT is in a conducting state.

6. The high voltage pulse generating circuit of claim 1, wherein said at least one conduction path comprises first and second diodes coupling said first and second terminals of said primary winding to said positive and negative terminals of said source of D.C. power.

7. The high voltage pulse generating circuit of claim 1, wherein the source of D.C. power is greater than 250 volts and less than 10 kV.

8. The high voltage pulse generating circuit of claim 1, wherein the sensing circuitry for generating a signal indicative of current flowing in the primary winding is a sensor.

9. The high voltage pulse generating circuit of claim 1, further comprising a pulse forming network coupled to the first and second terminals of the secondary winding, said pulse forming network including inductors with slugs, the slugs capable of varying an inductance of said pulse forming network.

10. A high voltage pulse generating circuit in a radiation treatment device, comprising:

a radiation source capable of generating a radiation beam having a variable radiation output;

a source of D.C. power having positive and negative terminals;

a flyback transformer having a primary winding and a secondary winding, said primary winding having first and second terminals configured to be alternately connected to and disconnected from said positive and negative terminals of said source of D.C. power; and sensing circuitry for generating a signal indicative of current flowing in said primary winding, said signal indicating the amplitude of said current;

wherein said source of D.C. power, said flyback transformer and said sensing circuitry are used to supply power to said radiation source such that said radiation beam is generated.

11. The high voltage pulse generating circuit in a radiation treatment device of claim 10, further comprising a solid state switching circuit for coupling said source of D.C. power to said primary winding of said flyback transformer in response to a control signal and for decoupling said D.C. power source from said primary winding in response to said signal indicating that a predetermined level of current was flowing in said primary winding.

12. The high voltage pulse generating circuit in a radiation treatment device of claim 11, wherein said solid state switching circuit comprises first and second IGBTs, said first IGBT coupling said first terminal of said primary winding to said positive terminal of said source of D.C. power when said first IGBT is in a conducting state, and said second IGBT coupling said second terminal of said primary winding to said negative terminal of said source of D.C. power when said second IGBT is in a conducting state.

13. The high voltage pulse generating circuit in a radiation treatment device of claim 11, wherein said solid state switching circuit further comprises first and second diodes coupling said first and second terminals of said primary winding to said positive and negative terminals of said source of D.C. power.

14. The high voltage pulse generating circuit in a radiation treatment device of claim 10, further comprising:

a pulse forming network coupled to said first and second terminals of said secondary winding; and a high voltage switch for shorting said pulse forming network in response to a shorting signal.

15. The high voltage pulse generating circuit in a radiation treatment device of claim 14, said high voltage switch including a plurality of SCR stages, each said SCR stage comprising an SCR, a resistor, and a control signal generator, said SCR having an anode, a cathode, and a gate, said SCR conducting current from said anode to said cathode in the presence of a control signal generating a potential between said gate and said cathode, said control signal being generated by said control signal generator, said resistor being connected between said anode and cathode, said stages being connected such that said SCR's are connected in series.

16. The high voltage pulse generating circuit in a radiation treatment device of claim 15, wherein said control signal generator in each said stage comprises a secondary winding of a pulse transformer, each said secondary winding being coupled to a common primary winding.

17. The high voltage pulse generating circuit in a radiation treatment device of claim 10, wherein said first and second terminals of said secondary winding are a pulse forming network, said pulse forming network including inductors with slugs, said slugs capable of varying an inductance of said pulse forming network.

* * * * *